US008365610B2

(12) United States Patent
Decraecker et al.

(10) Patent No.: US 8,365,610 B2
(45) Date of Patent: Feb. 5, 2013

(54) TESTING DEVICE FOR STRUCTURAL PANELS

(75) Inventors: Patrick Decraecker, Arsac (FR); Antoine Roussy, Bordeaux (FR); Romain Dubreuil, Bordeaux (FR); Olivier Mignon, Villenave d'Ornon (FR)

(73) Assignee: Astrium SAS, Paris (FR)

( * ) Notice: Subject to any disclaimer, the term of this patent is extended or adjusted under 35 U.S.C. 154(b) by 53 days.

(21) Appl. No.: 12/669,687

(22) PCT Filed: Jun. 18, 2008

(86) PCT No.: PCT/EP2008/057690
§ 371 (c)(1),
(2), (4) Date: Aug. 27, 2010

(87) PCT Pub. No.: WO2009/000721
PCT Pub. Date: Dec. 31, 2008

(65) Prior Publication Data
US 2010/0313670 A1    Dec. 16, 2010

(30) Foreign Application Priority Data

Jun. 25, 2007    (FR) .................................... 07 56002

(51) Int. Cl.
G01N 3/00 (2006.01)
G01N 3/10 (2006.01)
G01N 3/08 (2006.01)
G01M 5/00 (2006.01)
(52) U.S. Cl. ............ 73/802; 7/798; 7/794; 7/825; 7/837
(58) Field of Classification Search ............... 73/802, 73/849, 804, 841, 818, 794, 798
See application file for complete search history.

(56) References Cited

U.S. PATENT DOCUMENTS

| 6,381,546 | B1 * | 4/2002 | Starostovic ...................... 702/36 |
| 6,880,409 | B2 * | 4/2005 | Kawabe et al. ................. 73/856 |
| 6,931,942 | B2 * | 8/2005 | Uhlik et al. ..................... 73/853 |
| 7,155,982 | B2 * | 1/2007 | Oesmann et al. ............... 73/841 |
| 7,201,064 | B2 * | 4/2007 | Doak et al. ....................... 73/849 |
| 7,246,527 | B2 * | 7/2007 | Ostgaard et al. ................. 73/802 |
| 7,302,860 | B1 * | 12/2007 | Uhlik et al. ..................... 73/853 |
| 7,421,906 | B2 * | 9/2008 | Saves-Saint-Germes ...... 73/802 |
| 7,426,871 | B2 * | 9/2008 | Saves-Saint-Germes et al. ............................... 73/802 |
| 7,624,695 | B2 * | 12/2009 | Gotze et al. ................... 114/355 |

(Continued)

FOREIGN PATENT DOCUMENTS
FR    2889310    2/2007
FR    2889311    2/2007

OTHER PUBLICATIONS

Ambur Damodar et al., Design and Evaluation of Composite Fuselage Panels Subjected to Combined Loading Conditions; Journal of Aircraft, AIAA, vol. 42, No. 4, 2005; pp. 1037-1045.

(Continued)

*Primary Examiner* — Lisa Caputo
*Assistant Examiner* — Jonathan Dunlap
(74) *Attorney, Agent, or Firm* — RatnerPrestia

(57) ABSTRACT

A testing device for structural panels is characterized in that it includes passive apparatus in the form of a mount and interface apparatus between the mount and the panel to geometrically apply stresses representing the stresses caused by the parts surrounding the panel during a normal utilisation thereof.

26 Claims, 7 Drawing Sheets

U.S. PATENT DOCUMENTS

| | | | |
|---|---|---|---|
| 8,024,981 B2* | 9/2011 | Hinrichs et al. | 73/802 |
| 2003/0192385 A1* | 10/2003 | Uhlik et al. | 73/852 |
| 2004/0069072 A1* | 4/2004 | Kawabe et al. | 73/841 |
| 2005/0109118 A1* | 5/2005 | Oesmann et al. | 73/841 |
| 2006/0101921 A1 | 5/2006 | Ostgaard | |
| 2006/0213281 A1* | 9/2006 | Doak et al. | 73/849 |
| 2007/0022821 A1* | 2/2007 | Saves-Saint-Germes | 73/802 |
| 2007/0068275 A1* | 3/2007 | Saves-Saint-Germes | 73/802 |
| 2009/0260449 A1* | 10/2009 | Hinrichs et al. | 73/802 |
| 2010/0186519 A1* | 7/2010 | Cerreta et al. | 73/802 |

OTHER PUBLICATIONS

Bakuckas J.G. et al., "Full-Scale Testing of Fuselage Panels"; 2001 IEEE Autotestcon Proceedings. IEEE Systems Readiness Technology Conference, Aug. 20-23, 2001.

International Search Report dated Aug. 19, 2008.

* cited by examiner

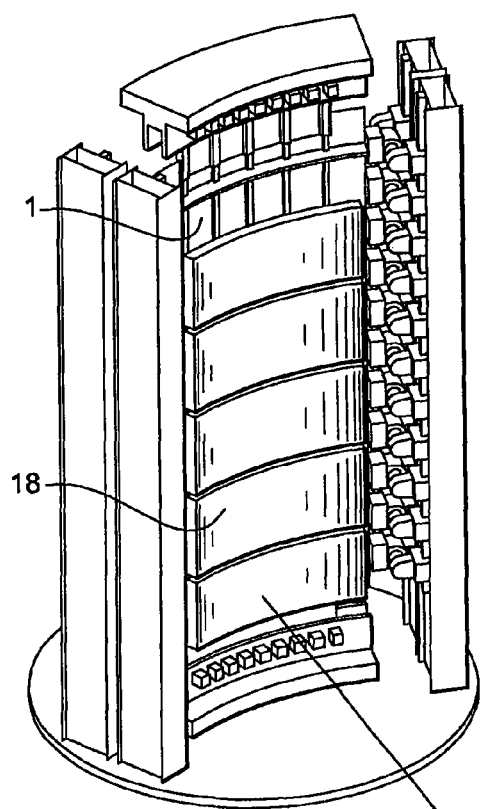
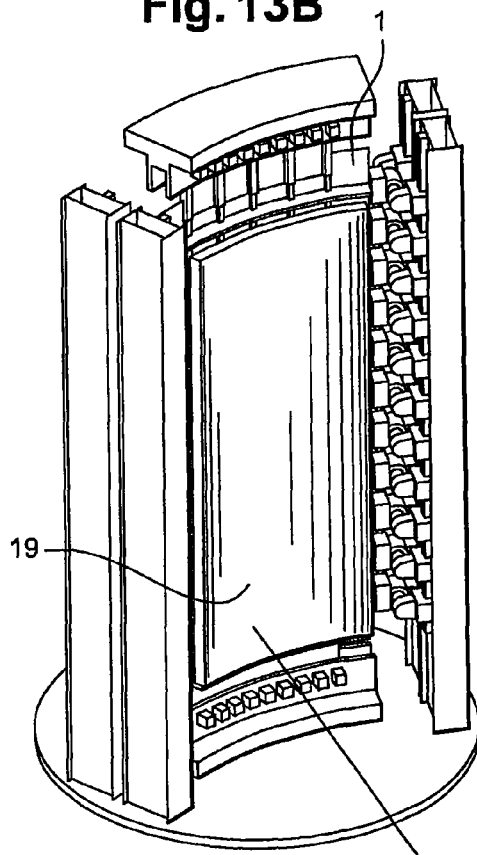
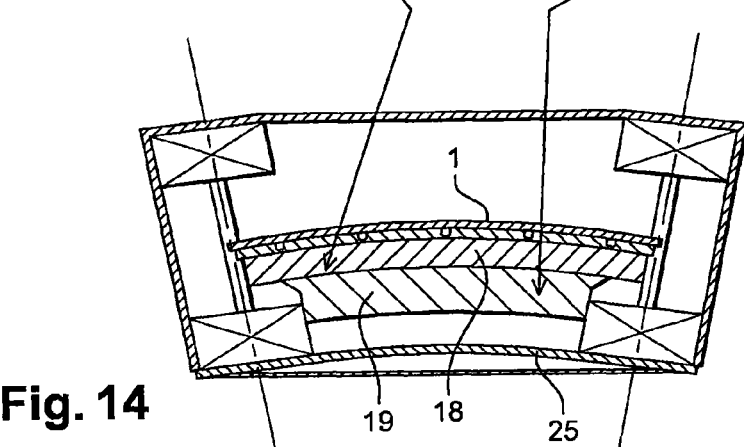

TESTING DEVICE FOR STRUCTURAL PANELS

This application claims priority of PCT International Application No. PCT/EP2008/057690 filed on Jun. 18, 2008. The contents of which are incorporated herein by reference.

FIELD OF THE INVENTION

The present invention relates to a testing device for structural panels.

BACKGROUND

The technical field concerned by the present invention is more particularly that of means for the mechanical testing of parts in full scale. These are tests during which parts in actual size are submitted to mechanical loads for which they have been dimensioned, either for checking that they really are capable of supporting such loads whether in the initial state, after ageing or after damage, or for certifying the same with respect to standards or regulations, or for determining the fatigue behavior thereof. Such tests are more particularly carried out for the certification of airplanes.

The invention more particularly relates to a testing means intended to stress curved panels, or more generally sectors of structures of revolution, such as fuselage elements or wing panels.

The tests to be carried out are very complex tests since they must simulate all the loads which an actual part is submitted to. This means that, in particular for a panel, transversal and axial stresses in traction and/or in compression, radial stresses (internal pressure in the plane), torsion and/or shearing, all in a combination must be provided while complying with the geometry of the structure of which the panel is an element.

Such tests can possibly be carried out under variable and controlled temperature and hygrometry conditions which are representative for example of the flight of an airplane, with temperatures from −70° C. up to +100° C., and hygrometry varying from 0 to 100% or under cryogenic or very hot conditions in the case of a space launcher.

The document US 2006/0101921 in the name of BOEING summarizes the problems to be faced for such simulations, i.e. radial simulations, shearing simulations combined with axial and transversal loads, radial stress and the necessity of carrying out numerical calculations and a complex piloting for simulating the behavior of panels at the interfaces thereof.

This document provides to provide all the stresses simultaneously under variable and controlled conditions and therefore describes various complex devices including the traction/compression system for the axial stress, a hydraulic displacement system of such traction system for applying shearing, membranes for enabling pressurization, a device including push links actuated by jacks driven by a computer to provide transversal loads.

This document describes a mechanically very complex device which requires sophisticated calculations to define the various stresses resulting from the various loads, more particularly to know the share of the transversal load.

The documents FR 2 889 310 and FR 2 889 311 provide testing segments of the whole fuselage to avoid the problems resulting from the tests on the panels. This makes it possible to use means which are easier to design and implement since when testing panels, the difficulty lies in the limit conditions and there are fewer limit conditions in a segment of the fuselage than in a panel of the fuselage. More particularly, the transversal loading problem no longer exists, and the radial loading can simply be simulated by the internal pressurization of the fuselage.

Such solutions which are applied to entire structures require gigantic and complex testing means which are totally out of proportion with respect to the tests to be carried out.

SUMMARY OF THE INVENTION

The object of the present invention is to define testing means for panels in full scale, making it possible to implement all the loads required in a simpler way than the existing known means.

For this purpose, the principle of the invention consists in replacing the mechanical transversal load by a geometric stress representing the complement of the panel to the structure which it is originating from.

For this purpose, the present invention provides a testing device for structural panels characterised in that it includes passive means in the form of a mount and interface means between the mount and the panel to geometrically supply stresses representing the stresses caused by the parts surrounding the panel during a normal utilization.

Preferably, the passive means include a load bearing mount including a base provided with a fixed beam receiving a first plurality of first interface means resting on the first longitudinal edge of the panel, at least two parallel mounts receiving a second plurality of second interface means resting on the side edges of the panel and the device includes a movable beam receiving a third plurality of third interface means resting on a second longitudinal edge of the panel, the movable beam being integral with means of traction and application of stresses to the panel, the testing device being so configured as to apply geometric stresses to the side edges of the panel according to the radius of curvature of the panel in response to a tensile strain on the second longitudinal edge of the panel applied with the means of traction and application of stresses to the panel.

Thus, according to the present invention, a plurality of active means imparting mechanical loads to the edges of the panel such as described in the document US 2006/0101921 are replaced by a geometry of the testing device so that it behaves as the actual environment of the panel being tested by applying geometric stresses thereto.

Advantageously, at least some of the interface means are configured to provide bonds between the mount and the panel offering a degree of freedom to these bonds between the mount and the panel in directions transversal to the edges of the panel.

BRIEF DESCRIPTION OF THE DRAWINGS

Other characteristics and advantages of the invention will appear upon reading the following description of a non limitative exemplary embodiment of the invention and referring to the drawings showing:

in FIGS. 13A, 13B: two perspective views of an exemplary embodiment of means for applying pressure onto a face of the panel according to one particular embodiment of the invention;

in FIG. 14: a schematic top view of the pressure application means of FIG. 13B.

DETAILED DESCRIPTION

Figure 1:
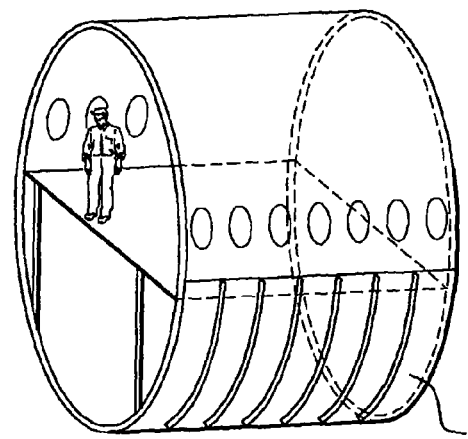
in FIG. 1: an exemplary structural panel tested with the device of the invention.
Figure 1:
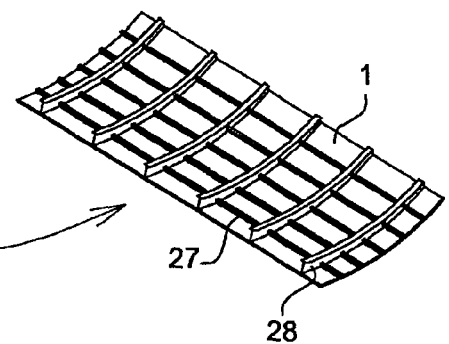

The device of the invention is more particularly suitable for carrying out mechanical tests on parts such as airplane structure panels 1 as shown in FIG. 1. The device is adapted for submitting such panels in natural scale to mechanical loads for which they have been dimensioned.

The panels include stringers 27 and frames 28.

In the case of airplane fuselage panels, the tests mentioned hereinunder as examples are more particularly required:

| | |
|---|---|
| Static tests | Pressure: Δp 2,000mb |
| | Traction stress: 4,000 KN |
| | Compression stress: flow max of 3,000 N/mm |
| | Shearing flow: 2,300 N/mm |
| Fatigue tests | Pressure: Δp 1,500mb |
| | Traction stress: 3,000 KN |
| | Compression stress: flow max of 3,000 N/mm |
| | shearing flow: 1,700 N/mm |

These tests are carried out between −70° C. and +100° C., fatigue tests are considered at a frequency of 0.2 HZ and the specimen deformation level resulting from the traction/compression loads is estimated at approximately ±10 mm.

Figure 2:
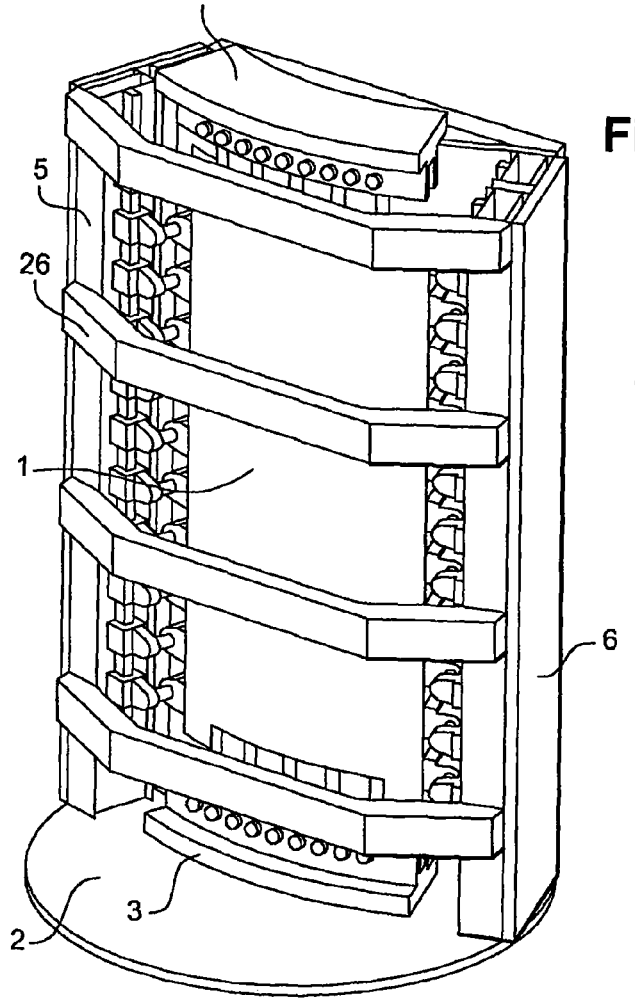
in FIG. 2: a perspective view of an exemplary embodiment of the device according to the invention.

The testing device for structural panels 1, a drawing of which is shown in FIG. 2, includes a load bearing mount including a base 2 provided with a fixed beam 3, at least two parallel posts 5, 6 and a movable beam 9.

Figure 3:
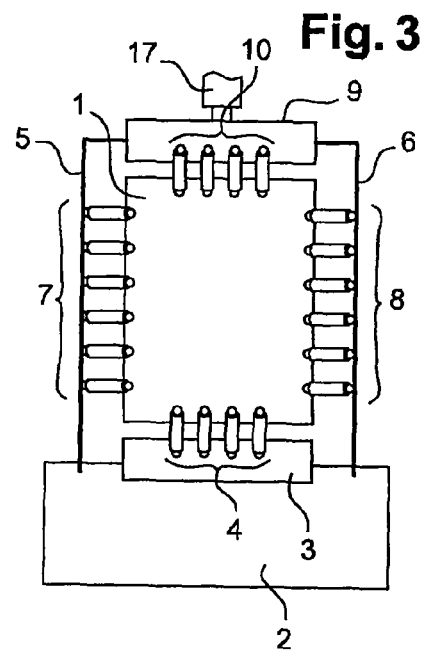
in FIG. 3: a schematic front drawing of the device of the invention provided with a panel to be tested.

As shown in FIG. 3, the fixed beam 3 receives a first plurality of first interface means 4 resting on a first longitudinal edge of the panel, the parallel mounts 5, 6 receive a second plurality of second interface means 7, 8 resting on the side edges of the panel, the movable beam 9 receives a third plurality of third interface means 10 resting on a second longitudinal edge of the panel and the movable beam 9 is integral with the means 17 of traction and application of stresses to the panel.

According to the invention, the testing device is geometrically configured for applying stresses to the side edges of the panel according to the radius of curvature of the panel in response to a traction or a compression stress applied on a second longitudinal edge of the panel applied with the means 17 of traction and application of stresses to the panel.

The device thus makes it possible to transmit axisymetric stresses while simulating the axisymetric limit conditions specific to a central segment panel in an airplane.

The device shown in FIG. 3 makes it possible to apply axial stresses in compression or in traction to the panel via the longitudinal interfaces of the panel linked to the stringers and to the skin of the panel while imparting a displacement to the panel according to the radius of curvature thereof via the side interfaces, as will be explained hereinunder.

Figure 7:
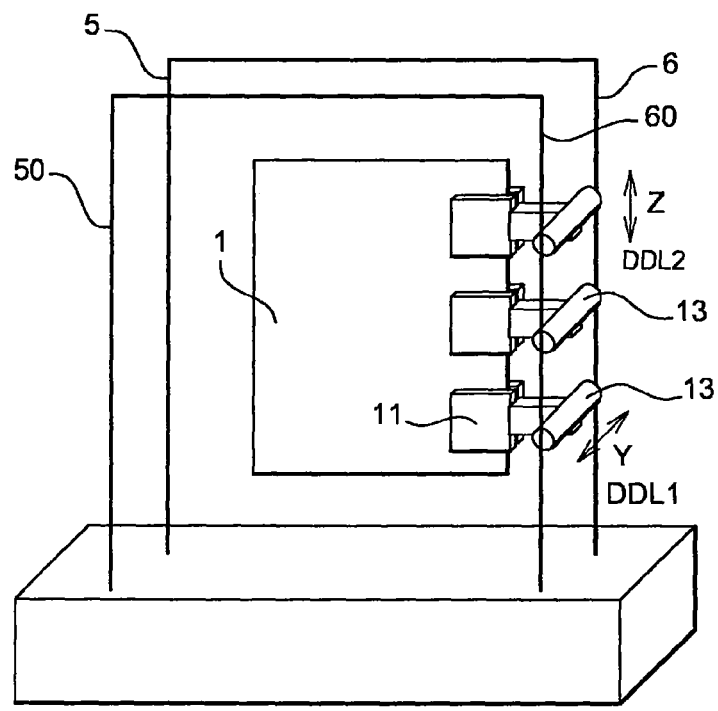
in FIG. 7: a schematic view of a bond between the panel and the post of the device.

FIG. 7 schematically shows two expected displacements of the second interface means with respect to the posts of the device.

According to this example, the interface means can move along two directions, a radial direction shown with a degree of freedom DDL1 along the axis Y and in line with the panel according to the degree of freedom DDL2 along the axis Z.

In this case, the second interfaces are placed on rails parallel to the posts making an axial free displacement of the tested structure possible.

These stresses and displacements are more particularly provided with the help of a particular configuration of the interface means and the bond thereof to the mount of the device.

Figure 6:
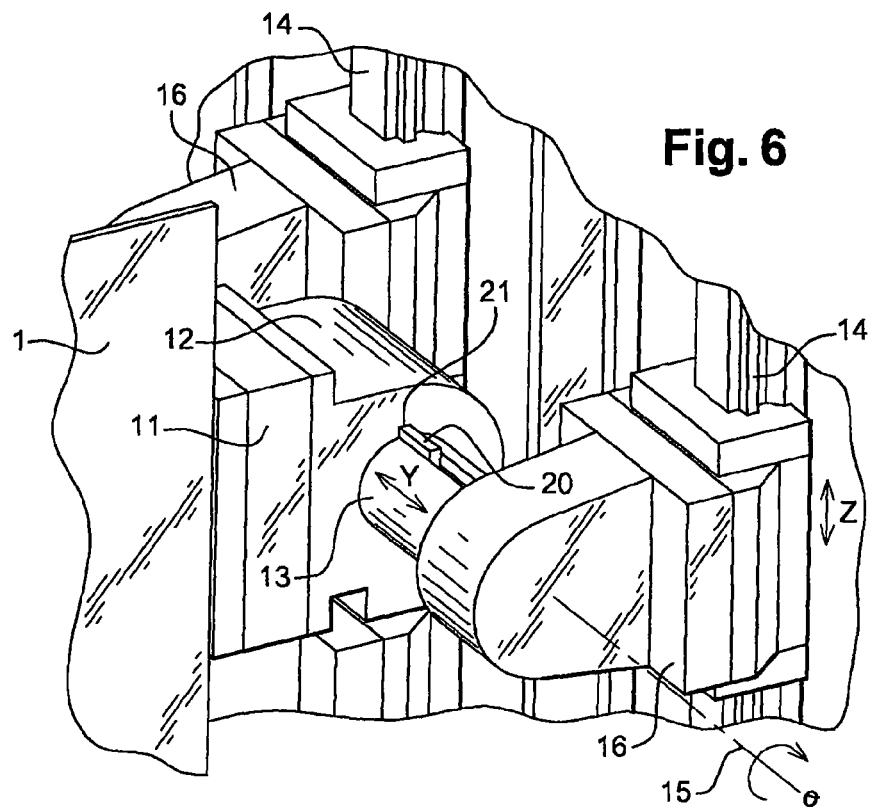
in FIG. 6: an exemplary embodiment of the interface means in compliance with the invention.

Such first, second and third interface means 4, 7, 8, 10, an example of which is shown in FIG. 6, include a plurality of fittings 11 positioned on the edge of the panel and regularly spaced from each other.

Figure 8:
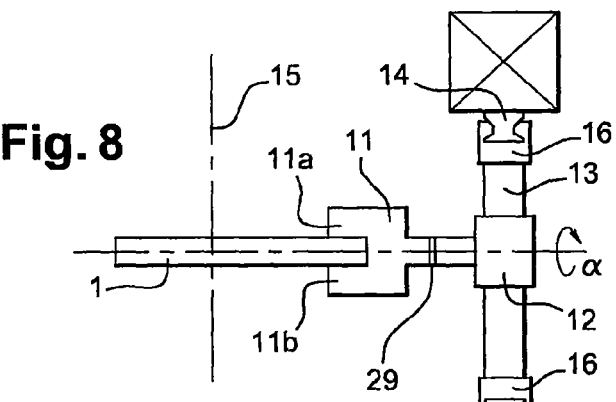
in FIG. 8: a schematic top view of a bond according to FIG. 7.

The fittings include for example jaws 11a, 11b schematically shown in FIG. 8 and glued or riveted onto the edges of the panel 1.

Figure 5:
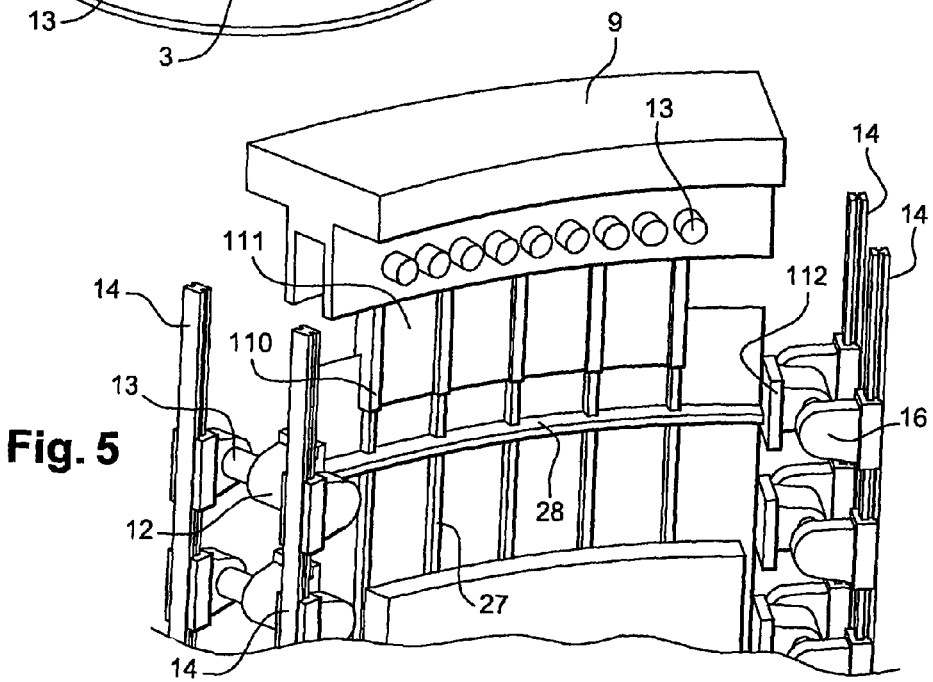
in FIG. 5: a detail of the device of FIG. 4 with the posts of the device being removed.

In the detail of FIG. 5 it can be seen that the fittings rest on the stringers 27: the fittings 110, on the skin of the panel: the fittings 111, and on the frames 28: the fittings 112.

Thus, all the attachments of the panel on matching panels surrounding the same are reproduced.

While referring back to FIG. 6, at least some other first, second and third interface means include clevises 12 mounted to slide on bars 13 resting on the mount.

At least some of the clevises 12, more particularly and preferably in the case of a balanced traction, with the clevises connecting the first interface means 4 resting on the first longitudinal edge of the panel with the fixed beam 3 and the clevises connecting the third interface means 10 resting on a second longitudinal edge of the panel to the movable beam 9, as well as the associated bars 13 include indexing means 20, 21 opposing a rotation of the clevises 12 on the bars 13.

The indexing means are advantageously movable, more particularly and preferably for the clevises connecting the second interface means 7, 8 with the posts which, in the absence of indexing means, gives a degree of freedom in rotation of the clevises 12 with respect to the bars 13 more particularly in the case of a shearing test.

The indexing means provided according to the example include keys 20 received in grooves 21 provided in the bars 13 as well as in the clevises 12.

Figure 9A:
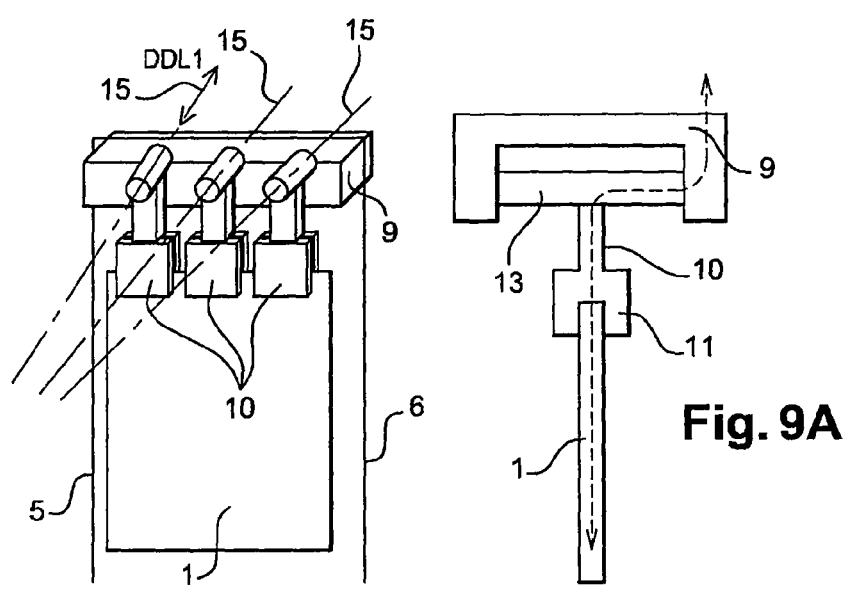
in FIGS. 9A and 9B: schematic views of bonds between the panel and the movable beam of the invention.
Figure 9B:
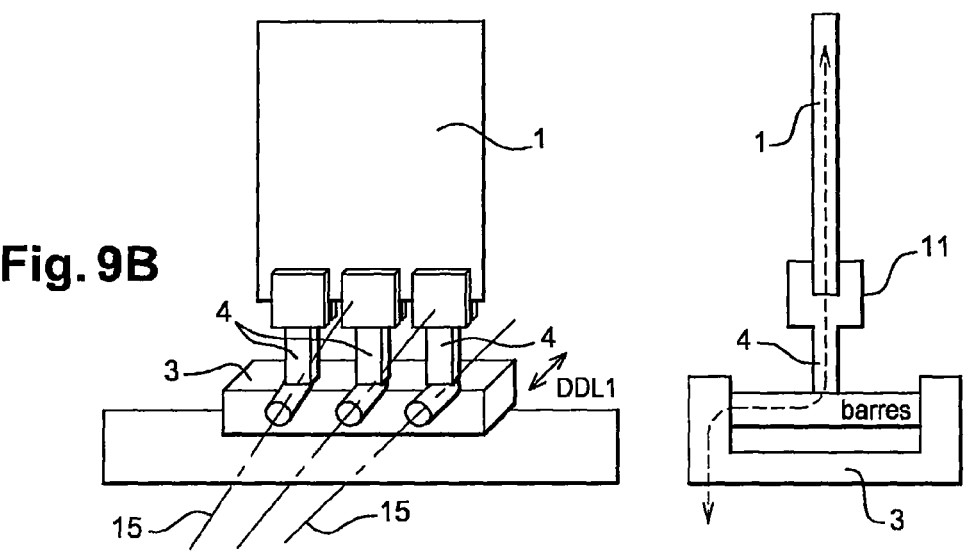

The first and third longitudinal interface means at the top and at the bottom are shown schematically in FIGS. 9A and 9B.

They aim at making the transfer of the loads possible while providing a radial guiding of the structure. They give a radial degree of freedom DDL1 to the interface means, the transfer of the traction loads from the panel to the base and hold the panel.

The beams 3 and 9 are U-shaped beams wherein the bars 13 bearing the interface means are inserted.

The longitudinal interface means are made of the fittings 11 connected to the panel and to a movable set with a radius of curvature composed by the bars 13 linked to the beams 3, 9.

Figure 4:
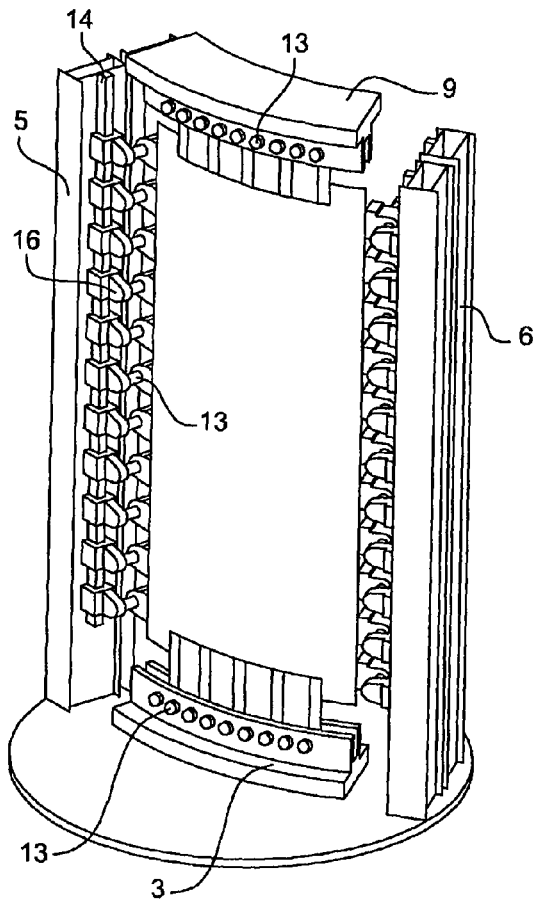
in FIG. 4: a perspective view of the device of FIG. 2, partially disassembled.

According to FIGS. 4 and 5, the movable beam 9 is bent in compliance with the radius of curvature of the panel. This is also true for the beam 3 linked to the base 2.

According to a preferred embodiment, the bars 13 are oriented in line with axes resting under the general identification coordinates 15 which are transversal to the panel and in the case of a panel having a curvature about a longitudinal axis (axis parallel to the plane linking the fixed beam and the movable beam) the axes 15 perpendicular to the panel are radial axes with respect to the panel, so as to avoid warping the panel during the application of longitudinal forces. The axes 15 are not parallel to each other when the panel is not planar, more particularly in the case of a curved panel of a fuselage segment. Similarly, the directions Y along the axes 15 are not parallel but distributed as per the radius of curvature of the panel.

In a particular configuration of the device of the invention shown in FIG. 4 and according to the detail in FIG. 5, the parallel posts 5, 6, 50, 60 are split and include load bearing slides 14, the side bars being integral with crossheads 16 mounted onto the load bearing slides 14.

Such split mounts are advantageously positioned with respect to each other so that the side bars are perpendicular to the tangent at the edge of the panel.

In this schematic configuration seen from underneath in FIG. 8, each side bar includes crossheads 16 at both ends thereof and the posts are provided with two slides so that the bars 13 can move parallel to each other.

It should be noted that, to have a better presentation of the ideal theoretical model, it is necessary to free the rotation along the axis of the guiding bar, and therefore the junction between the fittings 11 and the clevises 12 preferably includes a hinge 29 enabling a rotation a of the clevis with respect to the fittings along an axis going through the clevis and the fittings and perpendicular to the axis of the bar 13.

This configuration, for which the bars connected to the posts can move parallel to each other, is particularly suitable for traction and compression tests, with the hinges 29 making it possible to see the warping defects of the panel.

Figure 10:
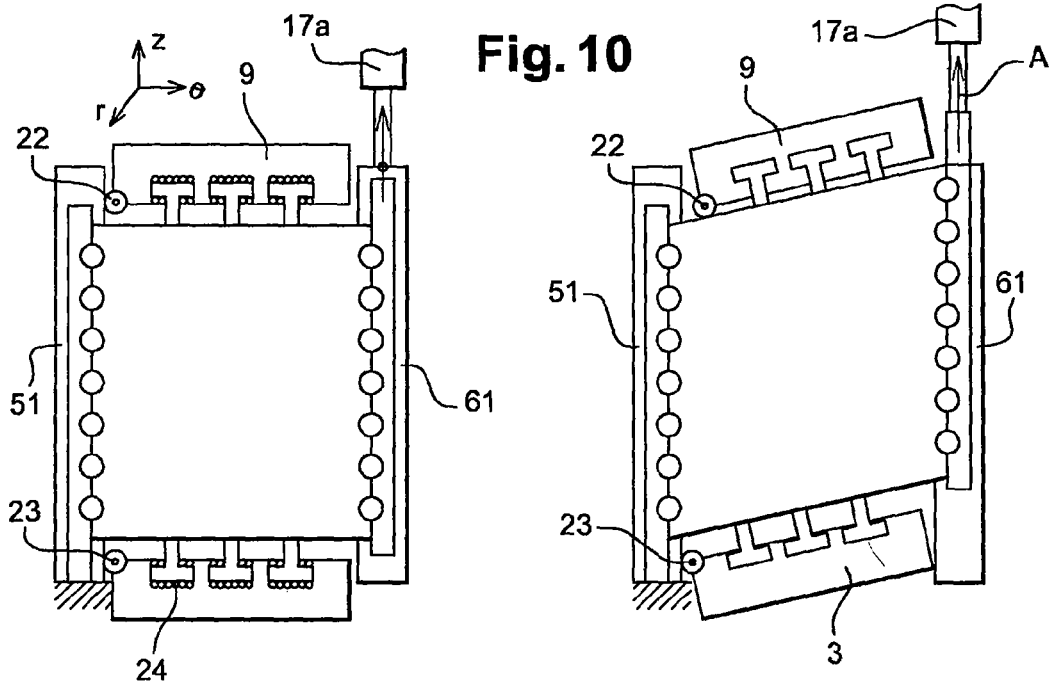
in FIG. 10: a schematic front view of a particular embodiment of the invention adapted to the application of shear stresses onto the panel.

The example in FIG. 10 corresponds to shearing tests.

In this case, the lateral bars are fixed with respect to the posts 51, 61 with at least one of them 61 being movable in translation along its axis A so that it can apply shear stresses to the side edges of the panel when a dissymmetric traction is applied by a jack 17a onto this post.

In this configuration, the device further includes axes 22, 23 about which the fixed beam 3 and the movable beam 9 can rotate upon the application of a traction on the post receiving the jack 17a.

Figure 11:
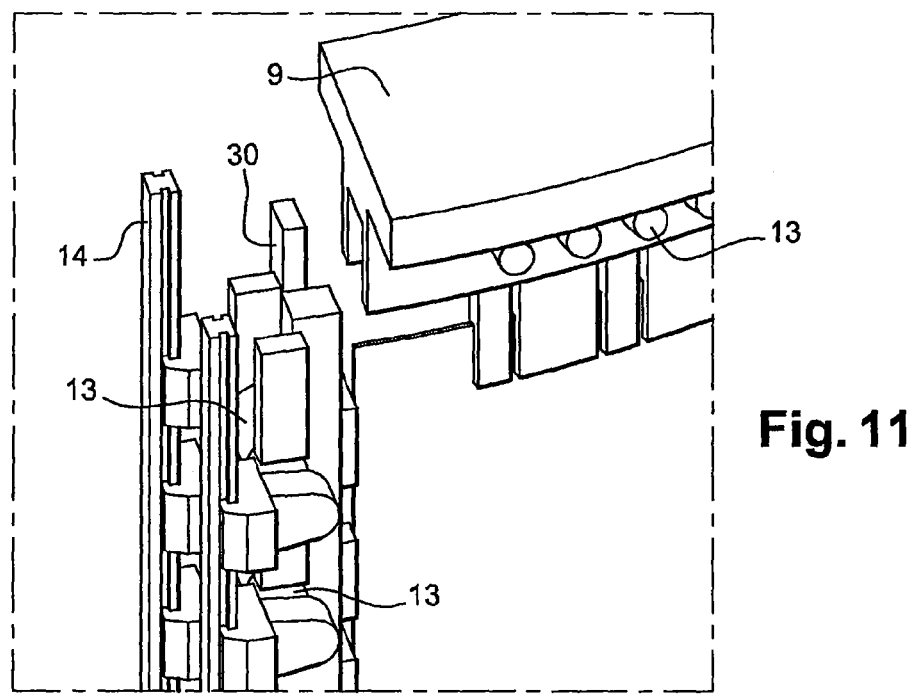
in FIG. 11: a perspective view of the detail of the embodiment of the device of the invention adapted to shearing test.

An embodiment based on the utilization of combs 30, which are movable and block the bars 13 for the shearing test, is shown in FIG. 11.

In this case, the jack 17a is advantageously integral with the comb or the combs blocking the bars on the device slide.

Similarly, according to the diagram of FIG. 10, for the shearing tests, the first and third interface means include at their bond with respectively the fixed beam 3 and the movable beam 9 raceways 24 in a direction parallel to the longitudinal direction of said beams, so that the interface means remain parallel to the longitudinal direction of the panel when a dissymmetric traction is applied to the movable beam on the side opposite the axis 22.

In both these cases and according to the principle of the invention, at least some of the interface means 4, 7, 8, 10 are configured so as to provide bonds between the mount and the panel offering a degree of freedom to such bonds between the mount and the panel in a direction Y transversal to the panel.

This is provided by the bonds of the clevises and the bars along which the clevises may slide on the bars along the axis generally identified by Y, as shown in FIG. 6, it being understood that the axes Y are local axes at each bar and are not necessarily parallel to each other.

In addition, at least some of the interface means 4, 7, 8, 10, when they correspond to the example of FIG. 6 and are free of indexing means provide bonds between the mount and the panel offering a degree of freedom in rotation (Θ) to such bonds between the mount and the panel about the axes 15 transversal to the panel which are the bars 13.

FIGS. 12A to 12F illustrate the possibility of blocking or releasing the degrees of freedom of the panel as a function of the tests to be carried out.

Figure 12A:
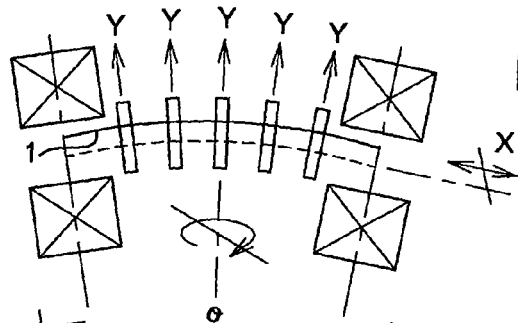
in FIGS. 12A to 12F: schematic representations of the loads and stresses applied to the panel respectively at the movable beam, and the mounts under the application of a traction or a compression, shearing and under the application of pressure on one side of the panel.
Figure 12B:
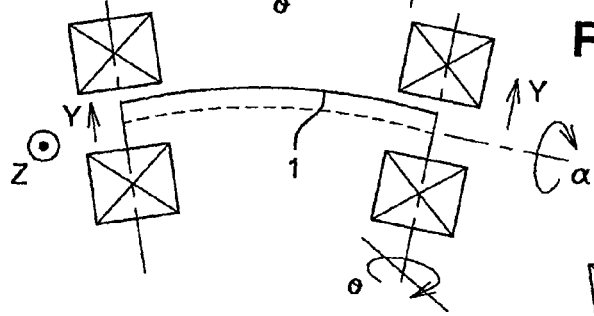

FIGS. 12A and 12B correspond to the traction or compression tests.

FIG. 12A shows the displacements of the first or third interface means, i.e. the means linking the panel to the lower beam 3 or to the upper beam 9 in the case of such tests.

In this case, the clevises and the bars are provided with indexing means and a rotation θ of the clevises on the bars is prohibited.

Similarly, an ortho-radial movement along an axis X (a curved axis according to the width of the panel) is impossible.

The sliding of the clevises on the bars is authorized (DDL1 is free) and a radial movement shown by the arrows Y is possible.

The displacement of the panel 1 is shown in the case of a compression test with respect to the initial position in dotted line.

As a matter of fact, in the case of a longitudinal compression (pressure on the movable beam), the panel tends to widen.

In the case of a traction test, the panel would tend to contract laterally and would move to the other side of the dotted line.

FIG. 12B shows the interface means positioned on the posts.

For these means, the displacement of the side interface means according to the vertical axis Z is authorized, the displacement of the clevises on the bars according to the axis Y is authorized and the rotation a of the fittings with respect to the clevises is authorized.

But here the indexing means are used and the rotation θ of the clevises on the bars is not possible.

Figure 12C:
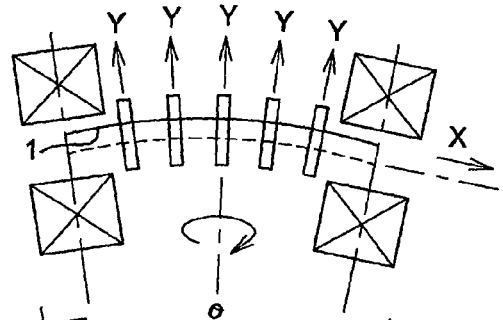
Figure 12D:
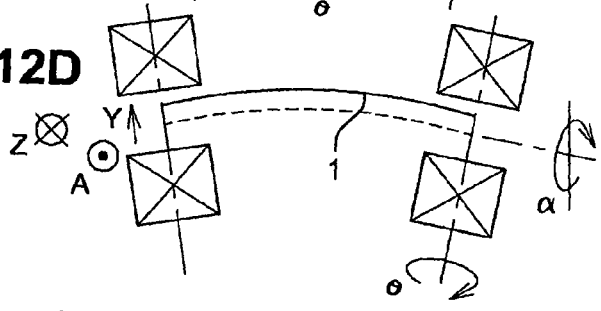

FIGS. 12C and 12D show the possible displacement of the panel within the scope of a shearing test.

For this test, the indexing means are removed from the movable beam shown in FIG. 12C which releases the rotation θ of the clevises on the bars.

Here again the radial movements along the axis Y (degree of freedom DDL1) are possible as well as the displacements of bars in the ortho-radial direction along the axis X while using the rolling means 24 in FIG. 10.

As regards the interface means on the posts as shown in FIG. 12D, the clevises on the bars are also released by removing the indexing means which enables the rotation θ of the clevises on the bars but the hinges between the clevises and the fittings are blocked, which prevents the rotation a of the fittings with respect to the clevises.

In addition, the free movements of the bars on the posts along the axis Z are prohibited and only one entire post moves along the axis A as already described in FIG. 10.

Figure 12E:
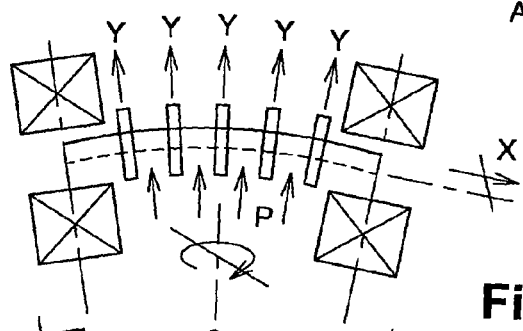
Figure 12F:
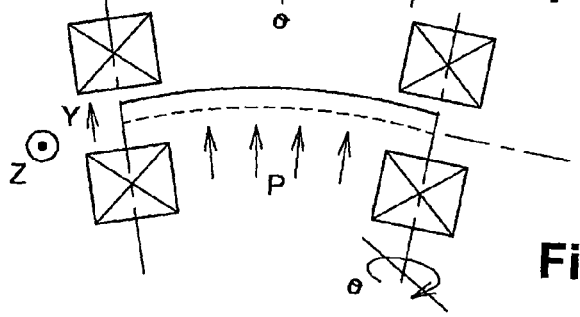

FIGS. 12E and 12F correspond to the panel pressurization test.

For these tests, the interface means with the upper and lower beams are blocked in rotation 8 by the utilization of the indexing means, the displacement along the axis X is blocked, only the displacement along the axes Y is possible.

Similarly, for the side interface means schematically seen in FIG. 12F, the rotation θ of the clevises about the bars is blocked and the displacement Z of the bars parallel to each other is released.

Then, according to all the tests, at least one of the interface means is configured to provide bonds between the mount and the panel thus offering a degree of freedom to such bonds between the mount and the panel along directions Y transversal to the edges of the panel.

In the case of traction/compression tests, the loads are transmitted to the structure via the longitudinal interfaces at the level of the beam. Such interfaces transmit a maximum flow of stress of 4,000 kN on a curvilinear length of 1.2 m for a curvilinear panel 2,600 mm in length and 1,200 mm in width.

The limit conditions provided by the interface of the edges of the panel make it possible to transmit the loads on the line provided while guiding the structure along the radius of curvature.

The displacements are of the order +/−10 mm axially and +/−10 mm radially.

Thus, according to the present invention, for a panel originating from an axially loaded structure of revolution, the problem consists in giving the sides of the panel parallel to the axis of revolution the possibility of moving radially first, only.

In reaction, the interface system applies the adapted stresses on these sides without needing mechanical element or sophisticated calculations.

The radial displacement results from the trend of the panel to shrink transversally under the application of a longitudinal traction, and to widen transversally under the action of a longitudinal compression.

One of the main mechanical characteristics of a panel of the fuselage of an airplane is the resistance thereof to the pressure stresses caused by the pressurization of the aircraft, which corresponds to the tests shown in FIGS. 12E and 12F.

To simulate this pressure, the device is provided with at least one bladder 18, 19 opposite the concave face of the panel 1.

This bladder is positioned so as to be able to apply pressure on the panel when it is inflated.

According to FIGS. 13A, 13B and 14, two bladders are used, a first bladder being shown in FIG. 13A in contact with the panel and separated into several elements as a function of the internal profile of the panel which includes strengtheners made of stringers in the longitudinal direction and frames in the transversal direction.

The specimen must be able to be submitted to pressure stresses (P of 2,000 mb) with the application of pressure on the side where the strengtheners for the stringers 27 and the frames 28 are positioned.

The internal particularities resulting from the presence of strengtheners for the frames and the stringers are taken into account for one or several secondary bladders 18 which are very flexible, which makes it possible to perfectly follow the shape of the strengtheners and thus to fill the various parts of the panel.

With a second bladder 19 or main bladder, as shown in FIG. 13B, and positioned between the locking plate 25 shown in FIG. 14, and extending along the panel on the whole height thereof, the secondary bladders 18 make it possible to apply pressure onto the whole specimen.

The various bladders are inflated with water for the room temperature tests and with a silicon oil for tests above +90° C. and the pressurization is obtained through a water/air exchanger controlled by a regulation device. This principle of water insulation makes it possible to limit security problems connected with air pressurization and to improve the cycle frequencies.

The considered bladders 18, 19 are for example made of polychloroprene elastomer of the SH type, 2 mm in thickness and with an elongation at break of 250%.

According to the example shown, the device includes a plurality of bladders 18 inserted between the stringers and the frames of the panel and the bladder 19 inserted between said plurality of bladders and a locking plate 25.

Upon the inflation of the bladders, the panel is submitted to pressure on the internal face thereof and reacts by a radial displacement of the clevises on the bars which is complying with the forces undergone by the panel in an actual condition.

While referring back to FIG. 1, the mount must resist the forces applied and therefor, strengtheners 26 are provided between the posts 5, 6.

The invention claimed is:

1. A testing device for structural panels comprising passive means including a mount and interface means between the mount and the panel to geometrically apply stresses representing stresses caused by the parts surrounding the panel during a normal utilisation, wherein the passive means include a load bearing mount including a base, said mount being provided with a fixed beam receiving a first plurality of first interface means resting on a first longitudinal edge of the panel, at least two parallel mounts receiving a second plurality of second interface means resting on side edges of the panel and wherein said testing device includes a movable beam, receiving a third plurality of third interface means resting on a second longitudinal edge of the panel, the movable beam being integral with means of traction and application of stresses to the panel.

2. A testing device according to claim 1, wherein said testing device is configured to apply geometrical stresses to the side edges of the panel according to the radius of curvature of the panel in response to a tensile strain on the second longitudinal edge of the panel applied with the means of traction and application of stresses to the panel.

3. A testing device according to claim 2 wherein the first, second and third interface means include a plurality of fittings positioned on the respective first and second edges of the panel and regularly spaced from each other.

4. A testing device according to claim 3, for which at least some of the first, second and third interface means include clevises mounted to slide on bars resting on the mount, wherein the fittings and the clevises are linked by a hinge.

5. A testing device according to claim 2 for which at least some of the first, second and third interface means include clevises mounted to slide on bars resting on the mount.

6. A testing device according to claim 5 wherein the bars are oriented in line with axes transversal to the edge of the panel.

7. A testing device according to claim 6 for wherein the axes perpendicular to the panel are radial axes with respect to the panel.

8. A testing device according to claim 5 wherein at least some of the clevises and bars include indexing means opposing a rotation of the clevises on the bars.

9. A testing device according to claim 5 wherein the parallel mounts include load bearing slides, lateral bars being integral with crossheads mounted on the load bearing slides.

10. A testing device according to claim 5, wherein lateral bars are fixed with respect to the mounts, at least one of those being movable in translation along its axis so that it can apply shear stresses to the side edges of the panel.

11. A testing device according to claim 1, wherein at least some of the interface means are configured to provide bonds between the mount and the panel offering a degree of freedom to these bonds between the mount and the panel in directions transversal to the edges of the panel.

12. A testing device according to claim 1, wherein at least some of the interface means are configured to provide bonds between the mount and the panel offering a degree of freedom in rotation to these bonds between the mount and the panel about axes transversal to the panel.

13. A testing device for structural panels comprising passive means including a mount and interface means between the mount and the panel to geometrically apply stresses representing stresses caused by the parts surrounding the panel during a normal utilisation, said device including at least one bladder opposite a concave face of the panel and positioned so as to be able to apply a pressure onto the panel, and further including a plurality of bladders inserted between stringers and frames of the panel and a further bladder inserted between said plurality of bladders and a locking plate.

14. A testing device according to claim 13 wherein the passive means include a load bearing mount including a base, said mount being provided with a fixed beam receiving a first plurality of first interface means resting on a first longitudinal edge of the panel, at least two parallel mounts receiving a second plurality of second interface means resting on the side edges of the panel and wherein the device includes a movable beam, receiving a third plurality of third interface means resting on a second longitudinal edge of the panel, the movable beam being integral with means of traction and application of stresses to the panel, the testing device being configured to apply geometrical stresses to the side edges of the panel according to the radius of curvature of the panel in response to a tensile strain on the second longitudinal edge of the panel applied with the means of traction and application of stresses to the panel.

15. A testing device for structural panels comprising passive means including a mount and interface means between the mount and the panel to geometrically apply stresses representing stresses caused by the parts surrounding the panel during a normal utilisation, wherein said testing device is configured to apply geometrical stresses to the side edges of the panel according to the radius of curvature of the panel in response to a tensile strain on the second longitudinal edge of the panel applied with the means of traction and application of stresses to the panel, wherein the passive means include a load bearing mount including a base, said mount being provided with a fixed beam receiving a first interface means resting on a first longitudinal edge of the panel, at least two parallel mounts receiving a second plurality of second interface means resting on the side edges of the panel and wherein said testing device includes a movable beam, receiving a third plurality of third interface means resting on a second longitudinal edge of the panel, the movable beam being integral with means of traction and application of stresses to the panel.

16. A testing device according to claim 15, wherein the first, second and third interface means include a plurality of fittings positioned on the respective first and second edges of the panel and regularly spaced from each other.

17. A testing device according to claim 16, for which at least some of the first, second and third interface means include clevises mounted to slide on bars resting on the mount, wherein the fittings and the clevises are linked by a hinge.

18. A testing device according to claim 15, for which at least some of the first, second and third interface means include clevises mounted to slide on bars resting on the mount.

19. A testing device according to claim 18, wherein the bars are oriented in line with axes transversal to the edge of the panel.

20. A testing device according to claim 19, wherein the axes transversal to the panel are radial axes with respect to the panel.

21. A testing device according to claim 18, wherein at least some of the clevises and bars include indexing means opposing a rotation of the clevises on the bars.

22. A testing device according to claim 18, wherein the parallel mounts include load bearing slides, lateral bars being integral with crossheads mounted on the load bearing slides.

23. A testing device according to claim 18, wherein lateral bars are fixed with respect to the mounts, at least one of those being movable in translation along its axis so that it can apply shear stresses to the side edges of the panel.

24. A testing device according to claim 15, wherein at least some of the interface means are configured to provide bonds between the mount and the panel offering a degree of freedom to these bonds between the mount and the panel in directions transversal to the edges of the panel.

25. A testing device according to claim 15, wherein at least some of the interface means are configured to provide bonds between the mount and the panel offering a degree of freedom in rotation to these bonds between the mount and the panel about axes transversal to the panel.

26. A testing device according to claim 15, and further including a plurality of bladders inserted between stringers and frames of the panel and a further bladder inserted between said plurality of bladders and a locking plate.

* * * * *

UNITED STATES PATENT AND TRADEMARK OFFICE
CERTIFICATE OF CORRECTION

PATENT NO.       : 8,365,610 B2  
APPLICATION NO.  : 12/669687  
DATED            : February 5, 2013  
INVENTOR(S)      : Decraecker et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 295 days.

Signed and Sealed this
First Day of September, 2015

Michelle K. Lee
*Director of the United States Patent and Trademark Office*